(12) United States Patent
Koh et al.

(10) Patent No.: US 8,494,623 B2
(45) Date of Patent: Jul. 23, 2013

(54) METHOD AND APPARATUS FOR IN-VIVO PHYSIOLOGICAL MONITORING

(75) Inventors: Dorothea Koh, Novena (SG); Bryant Lin, Menlo Park, CA (US); Paul J. Wang, Saratoga, CA (US); Marie Guion-Johnson, Minneapolis, MN (US); Amin Al-Ahmad, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 901 days.

(21) Appl. No.: 12/481,422

(22) Filed: Jun. 9, 2009

(65) Prior Publication Data

US 2010/0036208 A1 Feb. 11, 2010

Related U.S. Application Data

(60) Provisional application No. 61/131,448, filed on Jun. 9, 2008.

(51) Int. Cl.
*A61B 5/0452* (2006.01)

(52) U.S. Cl.
USPC .......................................................... 600/515

(58) Field of Classification Search
USPC ..................... 607/40, 124, 133, 138; 600/515
See application file for complete search history.

(56) References Cited

U.S. PATENT DOCUMENTS

| | | | |
|---|---|---|---|
| 6,285,897 B1 * | 9/2001 | Kilcoyne et al. | 600/350 |
| 6,929,636 B1 * | 8/2005 | von Alten | 604/890.1 |
| 7,245,954 B2 * | 7/2007 | Glukhovsky | 600/350 |
| 7,654,985 B2 * | 2/2010 | Dinsmoor et al. | 604/174 |
| 7,946,979 B2 * | 5/2011 | Gilad et al. | 600/109 |
| 2002/0103424 A1 * | 8/2002 | Swoyer et al. | 600/350 |
| 2004/0133089 A1 * | 7/2004 | Kilcoyne et al. | 600/350 |
| 2004/0147816 A1 * | 7/2004 | Policker et al. | 600/300 |
| 2004/0193029 A1 * | 9/2004 | Glukhovsky | 600/361 |
| 2005/0090873 A1 * | 4/2005 | Imran | 607/40 |
| 2007/0225576 A1 * | 9/2007 | Brown et al. | 600/301 |

* cited by examiner

*Primary Examiner* — Eric D. Bertram
*Assistant Examiner* — Roland Dinga
(74) *Attorney, Agent, or Firm* — Evans & Molinelli PLLC; Eugene J. Molinelli

(57) ABSTRACT

A method is provided that includes providing a monitoring apparatus including one or more modules within a target cavity or lumen of a body. The one or more modules are provided within the target cavity or lumen in a first state in which the monitoring apparatus is configured to remain within the target cavity or lumen. The method further includes monitoring physiological conditions of the body using one or more sensors within the one or more modules, and providing the one or more modules in a second state in which the monitoring apparatus is configured to exit the target cavity or lumen.

12 Claims, 8 Drawing Sheets

METHOD AND APPARATUS FOR IN-VIVO PHYSIOLOGICAL MONITORING

CROSS-REFERENCE TO RELATED APPLICATION

The present application claims priority to U.S. Provisional Application No. 61/131,448, filed on Jun. 9, 2008, the entire contents of which are herein incorporated by reference.

BACKGROUND OF THE INVENTION

1. Field of the Invention

The present invention relates to physiological monitoring.

2. Discussion of the Background

Atrial Fibrillation (AF) is a common cardiac arrhythmia that is estimated to affect at least 2.2 million patients in the United States. Patients suffering from AF have a two to seven times higher risk of stroke, and the disease has been reported to account for approximately fifteen percent of all strokes that occur nationally. Currently, there exist a variety of treatments for AF. These include rate or rhythm control medications, cardioversion, and the catheter ablation of arrhythmogenic regions inside the heart.

The human heart normally beats between sixty to one-hundred beats per minute when a person is at rest. In AF, the heart's electrical signals do not travel through normal pathways, but instead spread throughout the atria in a rapid and disorganized fashion, which in turn can cause the atria to activate in a chaotic fashion.

The onset of cardiac arrhythmia may be accompanied by physical symptoms. For instance, common symptoms in AF patients may include palpitations, an irregular fluttering sensation in the patient's chest, shortness of breath, dizziness, or a sudden feeling of weakness. Nevertheless, it is also common for physical symptoms to be absent during the onset of certain arrhythmic episodes, and in such cases, these asymptomatic cardiac arrhythmias, though serious, may go unnoticed by the patients.

One of the difficulties associated with the follow-up of AF treatment procedures lies in accurately assessing the long-term burden of AF in patients. Long-term (i.e. greater than 1 month) follow-up of a patient's cardiac rhythm is crucial for the optimal management of AF patients, with regard to the assessment of treatment efficacy and to the potential discontinuation of anticoagulation therapy. Currently, physicians do not have any means of gathering detailed information over an extended period of time regarding the true burden of AF in patients that will enable them to accurately determine the success of a treatment procedure in patients.

Known monitoring devices have not been able to fully address this problem of long term and continuous cardiac monitoring. One such approach to this problem involves the use of a "cardiac event monitor." This solution includes the use of a portable electrocardiography (ECG) recording device that is carried by the patient and communicates with one or more wired electrodes that are worn under the patient's clothing, and are adhesively attached to the patient's skin. The device records the heart's electrical activity at the push of a button. Patients trigger the device when they first begin to feel signs or the onset of physical symptoms that signal an "event", such as dizziness, weakness, palpitations or light-headedness. The device is also capable of storing the patient's cardiac rhythm by recording a rolling "window" of ECG data, which can later be transmitted over phone lines for review by a qualified physician. One example of a cardiac event monitor is described in U.S. Pat. No. 7,117,031.

Unfortunately, the cardiac event monitor does not adequately address the need for long-term and continuous monitoring of a patient's cardiac rhythm during follow-up of a treatment. Current cardiac event monitors can only be worn for up to a period of thirty days, and removal of the device is required during certain patient activities such as swimming or bathing. This in turn renders the device as not being truly continuous in its monitoring of cardiac arrhythmia events. Second, because patients may undergo asymptomatic recurrences of their arrhythmia, the reliance of the event monitor on detecting only symptomatic episodes in patients (i.e., symptom triggered recordings) can result in inaccuracies during determination of the true effectiveness of a treatment.

Furthermore, it is often cumbersome for the patient to have to be constantly connected to a set of wires and chest electrodes throughout the day, and the device can be difficult for many patients to integrate into their active lifestyle. Finally, the continuous attachment of sticky electrodes to the patient's chest tends to cause skin irritation, which further exacerbates the issue of poor patient compliance.

SUMMARY OF THE INVENTION

The present invention advantageously provides a device that can be advanced, placed, detached and implanted into one or more body lumens or cavities to perform internal diagnostic or therapeutic functions.

In one embodiment of the invention, the device can be used for continuous monitoring and/or recording of a person's physiological signals (e.g., heart rate, cardiac electrical activity, heart sounds). Additionally, an embodiment of the present invention can advantageously provide a delivery portion that enables the advancing of the entire device through one or more body lumens and/or cavities. Furthermore, an embodiment can advantageously provide a user-controlled mechanism for detaching a detachable portion of the device from the entire device structure such that the detachable portion of the device can be placed and implanted within a body lumen or cavity. Also, an embodiment of the present invention can advantageously provide a user-controlled mechanism for deactivating the detachable portion of the device after it has been implanted for a given duration. Additionally, an embodiment of the present invention can advantageously communicate with an external device that can download, process, and store the sensed information from the device and transmit the data to a remote healthcare provider or user.

One of the purposes of the present invention is to overcome at least some of the problems described above in connection with the lack of long-term continuous monitoring of post-AF treatment success by providing a way in which both symptomatic and asymptomatic atrial fibrillation events can be sensed and recorded for an extended period of time.

In a preferred embodiment of the present invention, the detachable portion of the device comprises of a series of two or more modules that are connected together. These modules can be linked together by flexible interconnecting structures such that the entire device can be advanced easily and navigated within hollow body lumen(s). Upon placement into the target body lumen, the device can be shaped by the user and locked into a rigid form or state. Delivery of the device into the target body lumen can occur through a natural orifice, such as the person's mouth, nose or rectum. When the device is delivered to the target body lumen, it will be detached from the entire device structure through a mechanical release that can be user-controlled and/or triggered.

When the detachable portion of the device is implanted within the body lumen, the activation of the device can occur either automatically or be triggered by the user. In a preferred embodiment of the present invention, activation is automatically triggered upon deployment of the detachable portion of the device. After activation, one or more sensors contained within the modules can begin recording and sensing physiological signals. In a preferred embodiment, the device will be used to detect the occurrence of atrial fibrillation events through recording of heart sounds. In other embodiments of the present invention, sensors within the device can detect a variety of different physiological signals for a variety of different conditions. Examples of such physiological signals that can be detected can include cardiac electrical activity, temperature, flow rate measurements, chemical substrates and/or molecules, arterial pulsations with pressure measurements, and arterial pulsations using pulse oximetry. In a preferred embodiment of the device, a microphone will be used to detect and record heart sounds from within the stomach cavity.

In order to maintain long-term monitoring, the detachable portion of the device is configured to remain within the target body lumen to prevent the transit of the capsule through the rest of the gastrointestinal (GI) tract. During the period of placement within the body lumen, an external device can periodically or continually, and wirelessly receive transmitted information regarding the sensed information. This external device can process, store and further analyze the information. In a preferred embodiment of the present invention, this external device can take the form of a portable home base station or device such as a cellphone. This information can then be transmitted to a remote user or a healthcare provider in order to assess the AF burden of a patient through a variety of methods including, but not limited to, telephony and direct electronic transfer.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF EXEMPLARY EMBODIMENTS OF THE INVENTION

Figure 1:
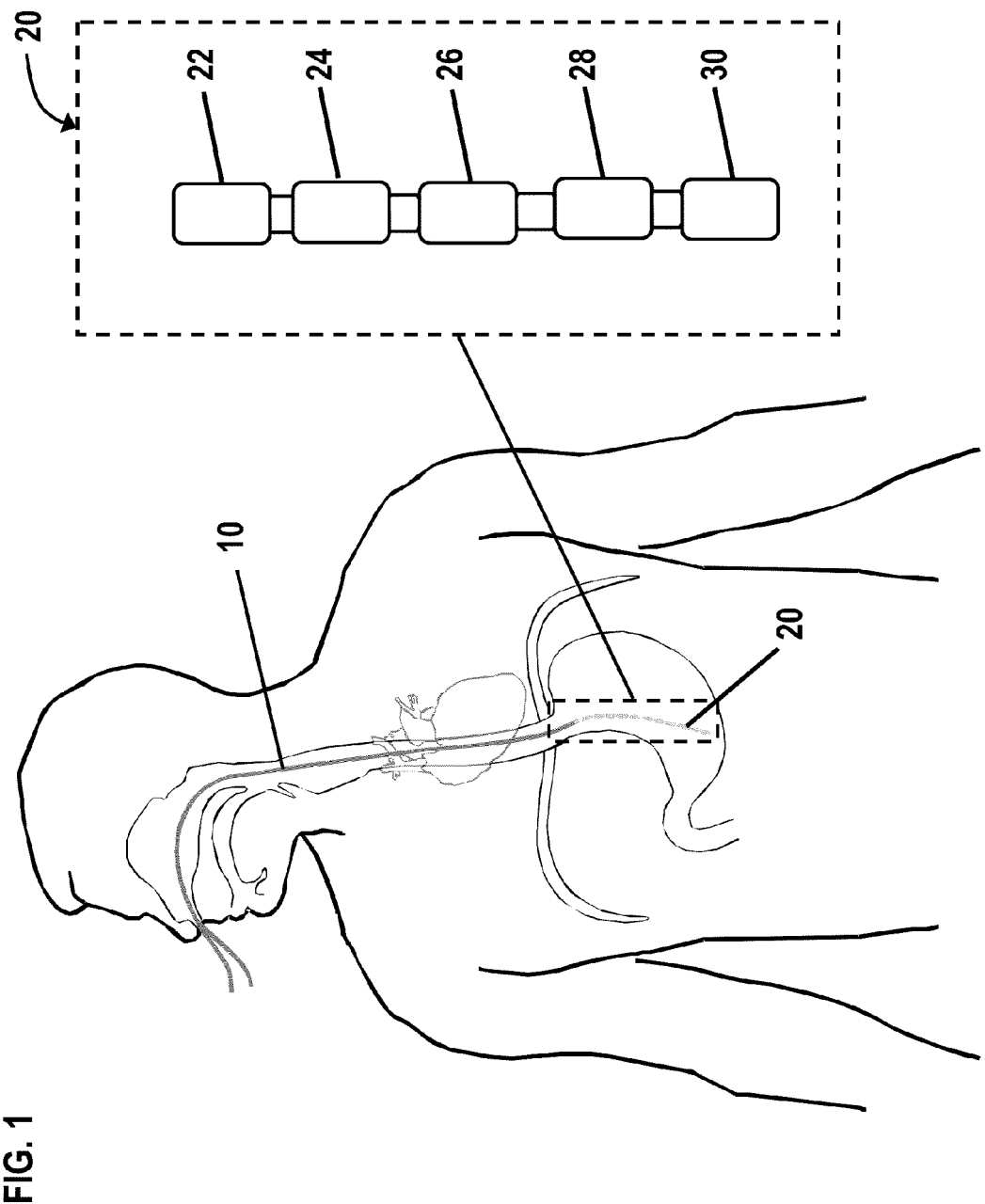
FIG. 1 is a schematic diagram of a delivery system for a monitoring apparatus and showing a partial, enlarged view of the monitoring apparatus, according to an embodiment of the invention.

Embodiments of the present invention will be described hereinafter with reference to the accompanying drawings. In the following description, the constituent elements having substantially the same function and arrangement are denoted by the same reference numerals, and repetitive descriptions will be made only when necessary.

The present invention provides a device that can be advanced, placed, detached and implanted within body lumens or cavities to collect and/or analyze physiologic data near to or from within body lumens or cavities, such as the gastrointestinal (GI) tract.

In the following description, various aspects of a preferred embodiment of the present invention will be described along with other possible variations in embodiments.

Reference is now made to FIG. 1, which illustrates a delivery system for a monitoring apparatus and showing a partial, enlarged view of the monitoring apparatus, according to an embodiment of the invention.

In a preferred embodiment of the present invention, the device comprises two main components: a delivery portion 10 and a detachable monitoring apparatus portion 20.

In a preferred embodiment, the delivery portion 10 and the detachable portion 20 are advanced through a natural orifice into the gastrointestinal tract of the patient until a target body lumen is reached. For example, in a preferred embodiment of the present invention, the device is advanced through the patient's nose through the esophagus into the patient's stomach cavity, as shown in FIG. 1. In other embodiments, the device can be advanced through other natural orifices such as the patient's mouth, nose, colon, or vagina. Alternatively, the device can be advanced through endovascular approaches through blood vessels such as veins or arteries. The device can be advanced into a variety of different body lumens or cavities, such as the lungs, heart, blood vessels, colon, GI tract, intestines, etc.

The delivery portion 10 of the device comprises of a flexible structure that allows for the easy advancement of the device the through body lumens and cavities. In a preferred embodiment of the present invention, the delivery component can take the form of a tubular-like structure preferably made of a material that remains innocuous to the tissues of the GI tract and the target body lumen. An example of a suitable material is silicon rubber.

FIG. 1 shows a partial, enlarged view of the detachable monitoring apparatus portion 20 in a state in which the detachable portion 20 can be inserted within a target cavity or lumen. The detachable portion 20 includes a series of modules that are flexibly interconnected to enable the advancement of the device through body lumens and cavities. The modules can contain a variety of different elements that can be used to sense and/or record physiologic data, or to perform subsequent analysis of the data recorded, or to communicate with remote device(s). For example, in the embodiment depicted in FIG. 1, the detachable portion 20 contains a sensing and/or recording module 22, a power source module 24, a processing module 26, a data storage module 28, and a transmitter/receiver module 30. In a preferred embodiment of the present invention, the series of modules are electrically connected to one another in order that data and information can be communicated between each module and another module within the series of modules. Other methods of communication can include Bluetooth, wireless transmission, infrared transmission, radiofrequency transmission, etc.

Figure 2:
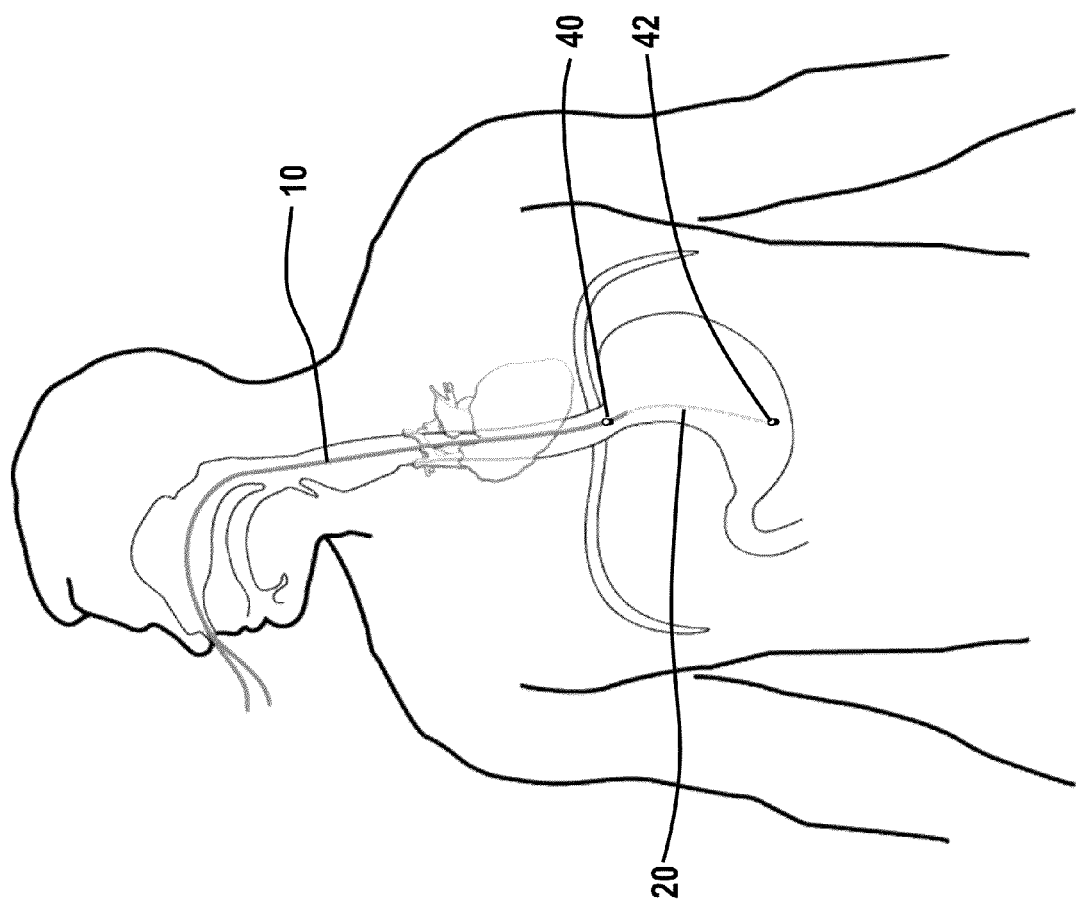
FIG. 2 is a schematic diagram of a delivery method for a monitoring apparatus using radio-opaque markers, according to an embodiment of the invention.

Reference is now made to FIG. 2, which shows the advancement of the device into the stomach of the patient through the nose. Successful delivery of the device can be determined through the use of fluoroscopy to visualize the presence of radio-opaque markers that can lie anywhere along the entire device structure. In a preferred embodiment of the present invention, a first radio-opaque marker 40 is provided at a proximal end of the detachable portion 20 of the device, and a second radio-opaque marker 42 is provided at a distal end of the detachable portion of 20 the device. The markers 40 and 42 allow a surgeon to monitor the advancement of the device through he patient's body, and to determine when the detachable portion 20 is properly positioned within the target cavity or lumen of the patient's body.

In other embodiments of the present invention, successful delivery of the device can be determined through one or more of the following means: the use of light emitting fluorescent dye; audio signals like beeping sounds or alarms that can be triggered by a detected pH level; magnetic guidance of the device as it is advanced into the target body lumen or cavity.

Figure 3:
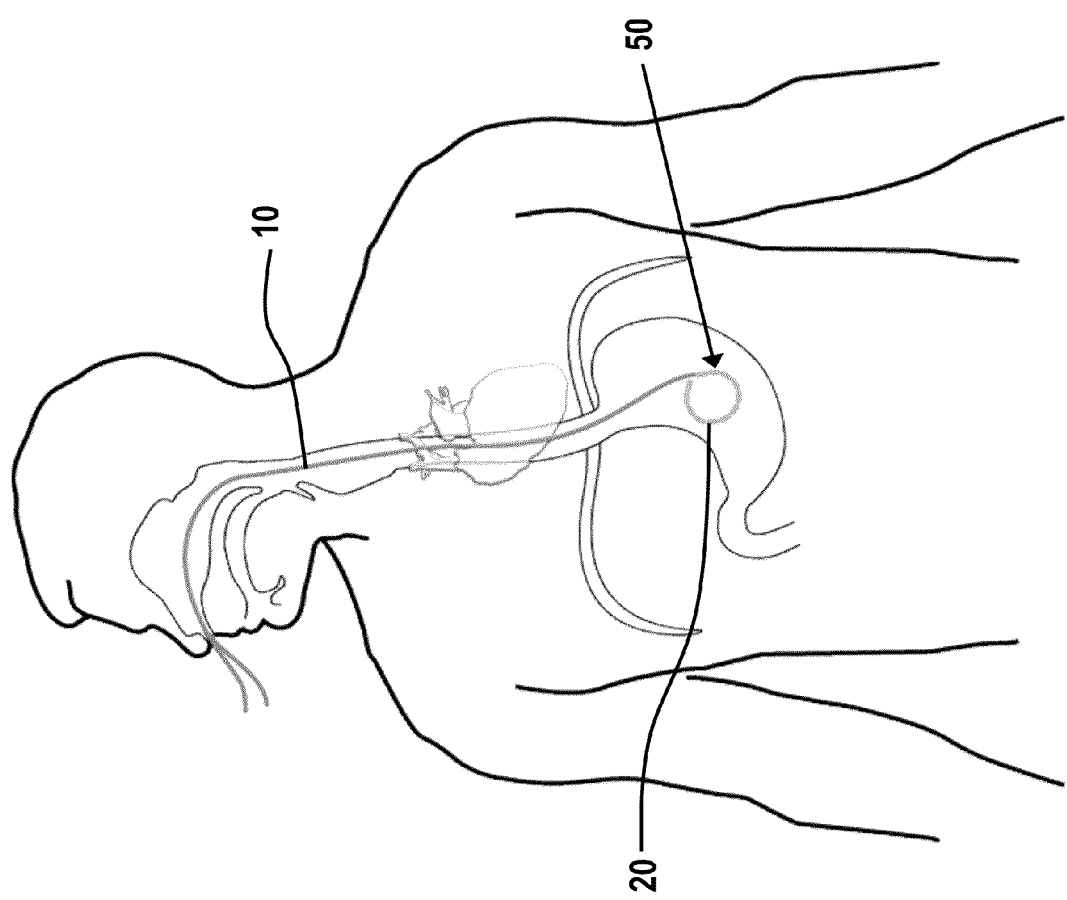
FIG. 3 is a schematic diagram of a delivery method for a monitoring apparatus where the monitoring apparatus is formed into a ring-like structure, according to an embodiment of the invention.

Reference is now made to FIG. 3, which shows a delivery method for a monitoring apparatus where the monitoring apparatus 20 is formed into a ring-like structure 50, according to an embodiment of the invention. In this embodiment, the detachable portion 20 of the device is shaped by the surgeon and locked preferably into a rigid ring-like structure 50. By forming the detachable portion 20 into a ring-like structure or state, the ring-like structure can ensure that the detachable portion 20 remains within the target body cavity or lumen during a period of time in which it is desired that the monitoring apparatus perform physiological monitoring, for example, by preventing the detachable portion from travelling further down through lower portions of the GI tract, which have a diameter less than that of the ring-like structure.

In a preferred embodiment of the present invention, a distal end of the delivery portion 10 is mechanically attached to a proximal end of the detachable portion 20 through a mechanical fastening/releasing mechanism.

Figure 4:
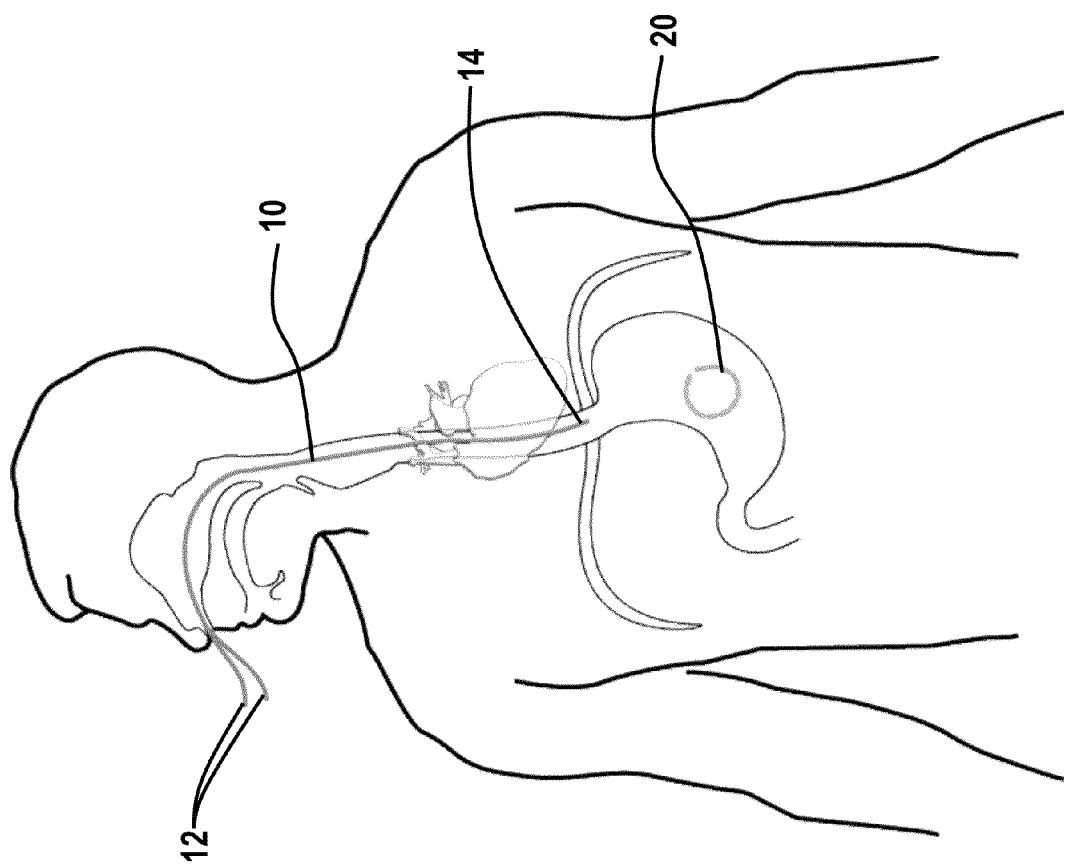
FIG. 4 is a schematic diagram of a delivery method for a monitoring apparatus where the monitoring apparatus is mechanically released and deployed into a body cavity, according to an embodiment of the invention.

Reference is now made to FIG. 4, which shows a delivery method for a monitoring apparatus where the monitoring apparatus 20 is mechanically released and deployed into a body cavity, according to an embodiment of the invention. After the detachable portion 20 of the device has been locked in the ring-like shape or state, then deployment of the detachable monitoring apparatus portion 20 into the target body lumen occurs through a user triggered mechanical release or detachment from the delivery portion 10. For example, a surgeon can use a triggering device (not shown) at a proximal end 12 of the delivery portion 10 to release a mechanical fastening/releasing mechanism at a distal end 14 of the delivery portion 10 in order to release the detachable portion 20 in the target cavity or lumen.

In various embodiments of the present invention, the delivery portion 10 of the device can include, but is not limited to, the following forms: a guide wire; a shape memory alloy material; a string or rope-like structure; a series of wires; a chain-like structure; a series of modular segments like pills or beads.

Alternative embodiments of the present application can utilize different deployment means that do or do not utilize a delivery portion 10. For example, the device can include an expandable structure contained within a pill capsule that can be swallowed by the patient and dissolved within the target body lumen to release the contained monitoring apparatus that can expand into an amorphous or pre-defined shape or state upon release. By expanding within the target body cavity or lumen, the expandable structure or state can ensure that the device remains within the target body cavity or lumen during a period of time in which it is desired that the monitoring apparatus perform physiological monitoring, and, after that time, the expandable structure can be deactivated into a deflated state to allow the monitoring apparatus to exit the body, for example, by natural means through the GI tract.

As shown in detail in FIG. 1, the detachable portion 20 of the device preferably comprises of a series of modules that are flexibly interconnected to enable the advancement of the device through body lumens and cavities. Each of the modules, 22, 24, 26, 28, and 30, can be configured to contain a different element used to allow the device to sense and/or record physiologic data, as well as to perform subsequent analysis of the data recorded. Additionally, in a preferred embodiment of the present invention, the series of modules are electrically connected to one another in order that data and information can be communicated between each module and other module(s) within the series of modules. Other methods of communication can include Bluetooth technology, wireless transmission, infrared transmission, radiofrequency transmission, etc.

The shape or locked-states of the detachable portion 20 of the device can be a variety of forms and structures. In a preferred embodiment of the present invention, as shown in FIGS. 3 and 4, for example, the shape of the detachable portion 20 is in the form of a ring-like structure or state 50 that is of appropriate dimensions in order to prevent obstruction to the GI tract. Other types of shapes or locked-states that the detachable component can be shaped in the form of include spherical, oval, donut-like, rectangular, patch-like, flat, curved, etc.

In addition, the shape of the various modules of the detachable portion 20 can include a variety of shapes and sizes. In a preferred embodiment, the modules 22, 24, 26, 28, and 30 are shaped in the form of pill capsules. Other embodiments can include spherical structures, oval structures, square structures, rectangular structures, etc.

Reference is now made to FIG. 1, which shows the modular components of the detachable portion 20.

The detachable portion 20 of the embodiment shown in FIG. 1 includes a sensing and/or recording module 22 that includes sensing and/or recording elements. Such sensing and recording elements can be contained within one or more of the modular segments to collect physiologic data from within the body lumen or cavity.

Figure 5:
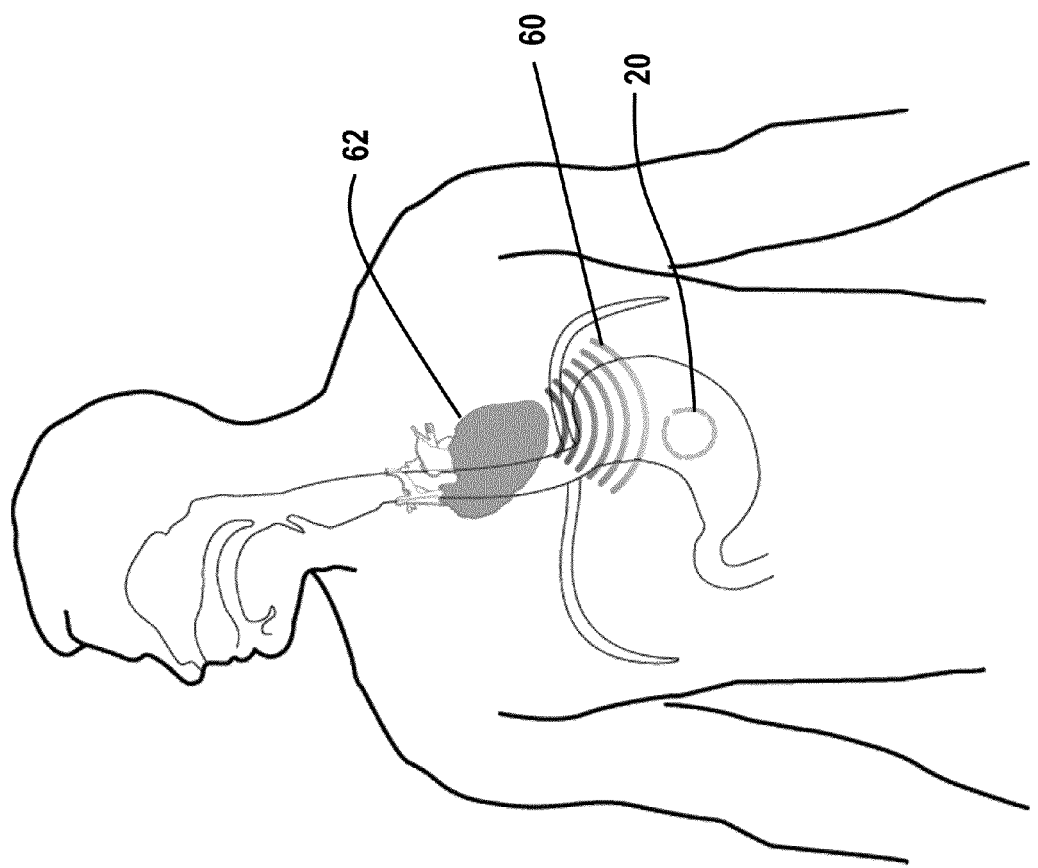
FIG. 5 is a schematic diagram of a monitoring apparatus sensing physiological signals, according to an embodiment of the invention.

Reference is now made to FIG. 5, which shows a monitoring apparatus sensing physiological signals, according to an embodiment of the invention. In FIG. 5, a sensing and recording module of the monitoring apparatus 20 is used to sense and record cardiac sounds 60 for a heart 62 of a patient. In a preferred embodiment of the present invention, the sensing and recording module includes a recording element in the form of a microphone that is contained within the module 22 to record and detect cardiac sounds in order to detect the number and duration of atrial fibrillation events. In another embodiment of the present invention, the sensing and recording module includes a sensor contained within the module 22 that includes an electrode that can detect cardiac electrical activity. Other methods of sensing cardiac rhythm can also include detection of arterial pulsations with pressure measurements from a pressure transducer, and detection of arterial pulsations using pulse oximetry.

It will be appreciated that a plurality of sensor element types can be used in the recording/sensing module 22 depending on the type of physiologic data being collected. These sensor element(s), can refer to any element suitable for sensing and/or recording data prevailing near or in the body lumen (e.g. GI tract), and that are capable of being appended to or included within the module. Examples of these sensor element(s) can include other acoustic sensors, pressure sensors, motion sensors, flow sensors, accelerometers, position sensors, infra-red sensors, optical detectors, electrical resistance sensors, electrical current sensors, electrical voltage sensors, etc.

Other variations in the type of physiologic data that can be detected and/or recorded by the monitoring apparatus can include acoustic or vibration signals, gastric sounds, normal or pathological heart sounds, electrical activity, flow, velocity, pressure, respiratory rate, breath sounds, nervous activity, muscle movements, peristaltic activity, chemical substrates, metabolic activity, etc.

Additionally, one or more of the modules in the detachable portion 20 can also include a sensor that can detect environmental changes to provide location or positional information. In another embodiment of the device, this sensor can be a pH sensor that can provide location information in tracking the capsule as it travels through the patient's body lumen or GI tract by sensing the environmental pH of the GI tract.

The detachable portion 20 of the embodiment shown in FIG. 1 further includes a power source module 24. The detachable portion 20 of the device can be powered by a power source within power source module 24 that can provide power to any electrical elements within the various modules of the detachable portion 20, such as the sensing and/or recording components within module 22. In a preferred embodiment of the device, the power source within module 24 is in the form of a rechargeable battery. Other examples of power sources that can be used to power the device can include: one or more batteries; lithium ion batteries; high density chemical batteries; high efficiency micro-batteries; removable batteries; electrochemical cells; super-capacitor storage units; fuel cells; metabolically driven cells; or any other suitable electrical power source.

The detachable portion 20 of the embodiment shown in FIG. 1 further includes a processing module 26. The processing module 26 in the detachable portion 20 of the device contains a signal processing system that can apply a variety of signal processing tools to the data recorded by the sensing/recording module 22. In a preferred embodiment, the processing module 26 can apply a series of noise filters to filter out one or more sources of noise in the acquired signal. Examples of noise that can be filtered include extraphysiological noises, breath sounds, GI peristalsis sounds, movement sounds, and any unrelated artifacts which can interfere with interpretation of the data.

In a preferred embodiment of the present invention, the processing module 26 also analyzes the sensed/recorded data for atrial fibrillation events. This is preferably accomplished through the one or more of the following ways: detection of atrial contraction heart sounds (e.g. S4); variability in the amplitude of the S1 heart sound; S2 heart sounds; detection of heart rate. In other embodiments of the invention, the processing module 26 can also perform analysis of an atrial fibrillation event through the detection of cardiac electrical activity, flow measurements, imaging of the heart.

In another embodiment of the present invention, the processing module 26 can perform one or more processing functions which can include data analysis, extraction of heart rate and heart sound information.

The detachable portion 20 of the embodiment shown in FIG. 1 further includes a data storage module 28. The physiological data collected by the sensor/recording module(s) 22 can be stored in raw or processed format within a data storage component located within a data storage module 28 of the device, so that further external download and assessment can be performed.

In a preferred embodiment of the present invention, data acquired by the sensing/recording module 22 will be transferred to the data storage module 28 and stored using a data storage unit, such as a Secure Digital High Capacity (SDHC) flash memory drive housed within the module 28, with the option of transmitting the data to an external device. In alternate embodiments, the data reception and storage components within the processing module 26 and the storage module 28 can be of another configuration. For example, the data processor unit and data processor storage unit can include magnetic data storage, optical storage, non-volatile computer memory, DRAM, SRAM, compact flash memory, SDHC flash memory, semiconductor memory chips.

The detachable portion 20 of the embodiment shown in FIG. 1 further includes a transmitter/receiver module 30. In a preferred embodiment of the present invention, one of the modules, namely module 30, in the detachable portion 20 contains an internal transmitter and/or antenna unit for the transmission of the collected data from the sensing/recording module 22 to a receiving unit. The transmitter/receiver module 30 can also control the activation of the sensing/recording components in the module 22 to a receiving unit. The transmitter of the transmitter/receiver module 30 can also control the activation of the sensing and recording elements within module 22 through communication with the other modules.

A suitable transmission component within module 30 can be any type of short-range or long-range wireless transceiver and/or transmitter that can communicate with an external transmitter and/or receiver unit of an external device that preferably outside of the body of the patient. Additionally in a preferred embodiment of the present invention, the transmitter/receiver module 30 can also receive data and control commands from the external device as described below.

Other examples of transmission components can include wireless microphones, Infrared Data Association (IrDA), Radiofrequency Identification (RFID), wireless USB, Dedicated Short Range Communications (DSRC), Near Field Communication, wireless light switches, Bluetooth, Ultra-Wideband.

Figure 6:
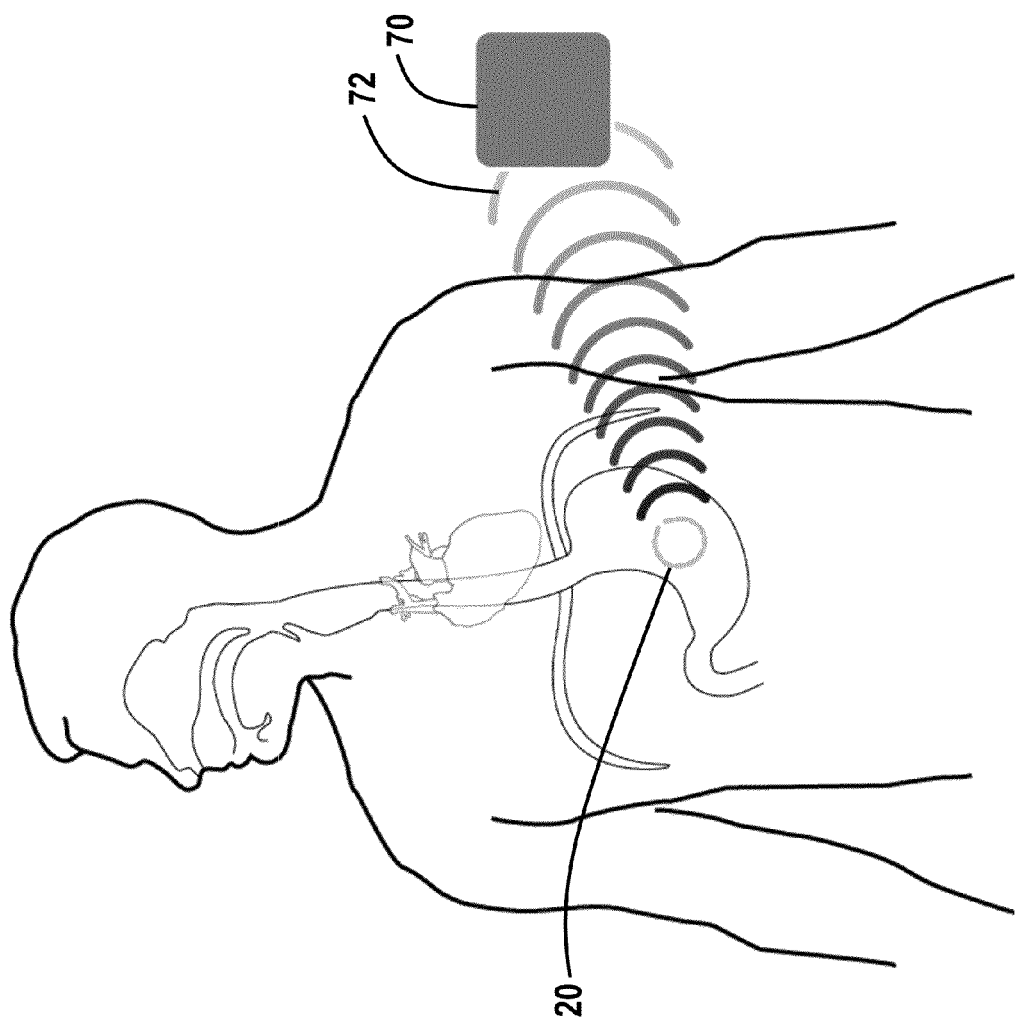
FIG. 6 is schematic diagram of a monitoring apparatus transmitting data to an external device, according to an embodiment of the invention.

FIG. 6 is schematic diagram of a monitoring apparatus 20 transmitting data to an external device 70, according to an embodiment of the invention. In a preferred embodiment of the present invention, the physiological data collected by the detachable portion 20 can be downloaded to an external device 70 for storage as well as further processing and analysis. The data can be downloaded through several different modes. In a preferred embodiment, the data is downloaded to the external device 70 through the use of a wireless transmission 72, such as a Bluetooth transmission. Other alternate embodiments can use a variety of transmission mechanisms, which can include radiofrequency transmission, infrared transmission, wireless transmission, etc.

The processed data from the external device 70 can be sent to a remote user or healthcare provider through one or more modes of communication. A suitable mode of transmitting this data can include electronic transmission over the internet. Other variations in communication can include direct electronic transfer, telephony, wireless transmission, etc. In another embodiment, the data can be transferred to a microprocessor found in handheld, workstation, or laptop computer. The data can also be further assessed by a healthcare professional in a remote location to determine if the person is experiencing atrial fibrillation which will require further medical intervention.

Figure 7:
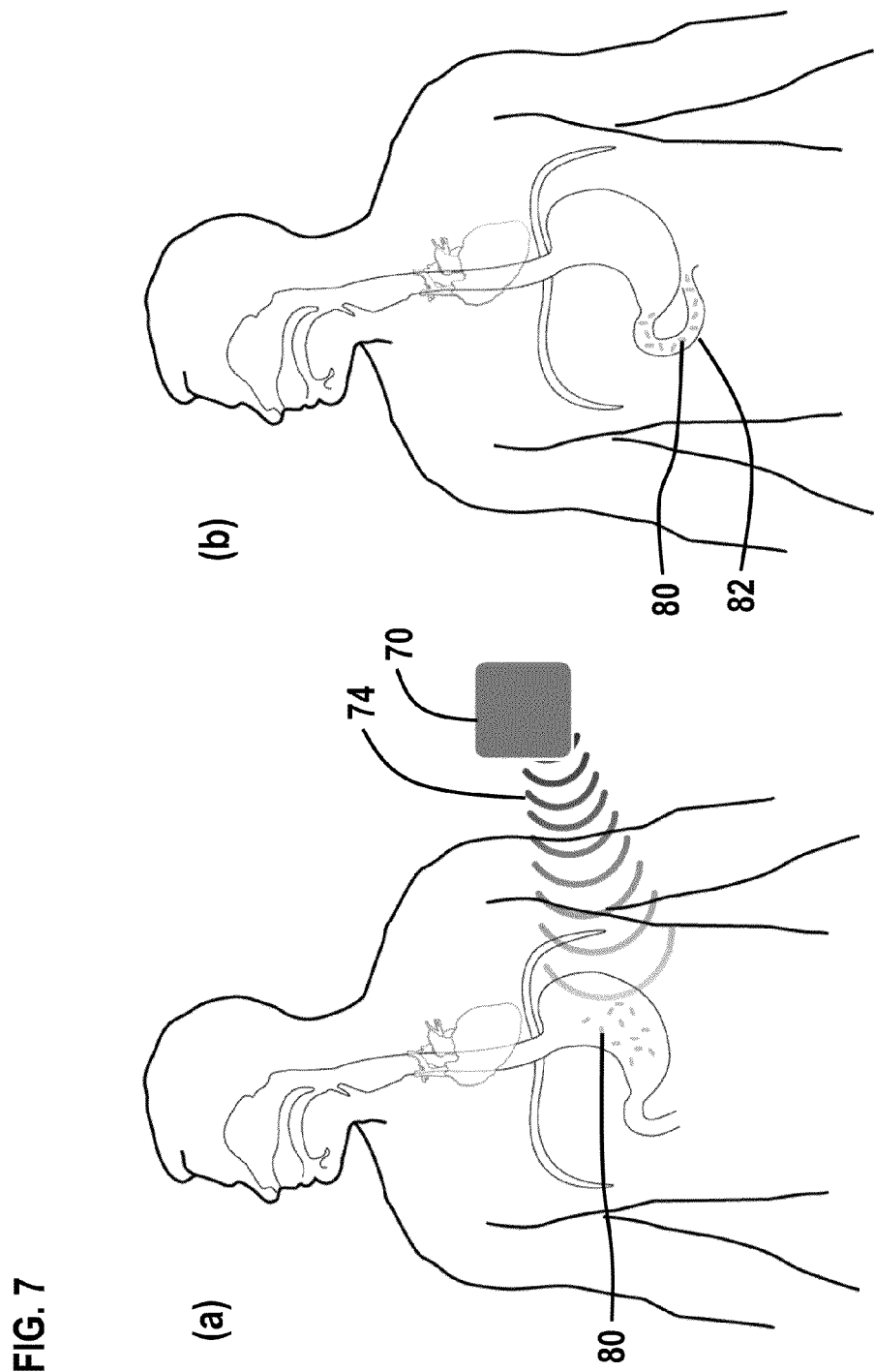
FIGS. 7($a$) and 7($b$) are schematic diagrams of a monitoring apparatus showing user-controlled deactivation of the monitoring apparatus, according to an embodiment of the invention.

FIGS. 7(a) and 7(b) are schematic diagrams of a monitoring apparatus showing user-controlled deactivation of the monitoring apparatus, according to an embodiment of the invention. FIGS. 7(a) and 7(b) show a user-controlled triggering mechanism of deactivation of the detachable portion 20. A user (e.g., doctor, nurse, patient, etc.) can deactivate the detachable portion 20 and terminate monitoring at the end of a monitoring period or at any point in time.

The detachable portion 20 of the device can be deactivated through one or more mechanisms. In a preferred embodiment of the present invention, the detachable portion 20 of the device is deactivated through a user controlled mechanical cutting of interconnecting links between the different modules 22, 24, 26, 28, and 30. For example, a user can trigger the release of a mechanical cutting tool from within the various modules by sending a wireless signal 74 from an external device 70 to the transmitter/receiver module 30 of the detachable portion within the body lumen. This allows the modules 22, 24, 26, 28, and 30 to split apart into individual pill capsules 80, as can be seen in FIG. 7(a), and in this state the capsules 80 are allowed to exit the stomach and pass through a lower portion 82 of the GI tract, as can be seen in FIG. 7(b), to be removed from the patient's body.

Other embodiments for user-controlled deactivation of the detachable device can include a wired or wireless signal that causes a heat-triggered deactivation, a light-triggered deactivation, a pH-triggered deactivation, or a sound triggered deactivation, for example, such a deactivation signal can be sent from one of the modules, such as sensing/recording module 22 or processing module 26, to the other modules. In another embodiment, automatic deactivation of the detachable device can occur through the timed degradation of biodegradable interconnecting structures between the modules, for example, such a deactivation signal can be sent from one of the modules, such as sensing/recording module 22 or processing module 26, to the other modules.

FIGS. 8(a)-8(g) are schematic diagrams of an entire cycle including implantation, usage, and deactivation of a monitoring apparatus, according to an embodiment of the invention. FIGS. 8(a)-8(g) contain stepwise schematic diagrams of an embodiment of a method of use of the device, where FIG. 8(a) corresponds to FIGS. 1 and 2, FIG. 8(b) corresponds to FIG. 3, FIG. 8(c) corresponds to FIG. 4, FIG. 8(d) corresponds to FIG. 5, FIG. 8(e) corresponds to FIG. 6, FIG. 8(f) corresponds to FIG. 7(a), and FIG. 8(g) corresponds to FIG. 7(b).

Figure 8:
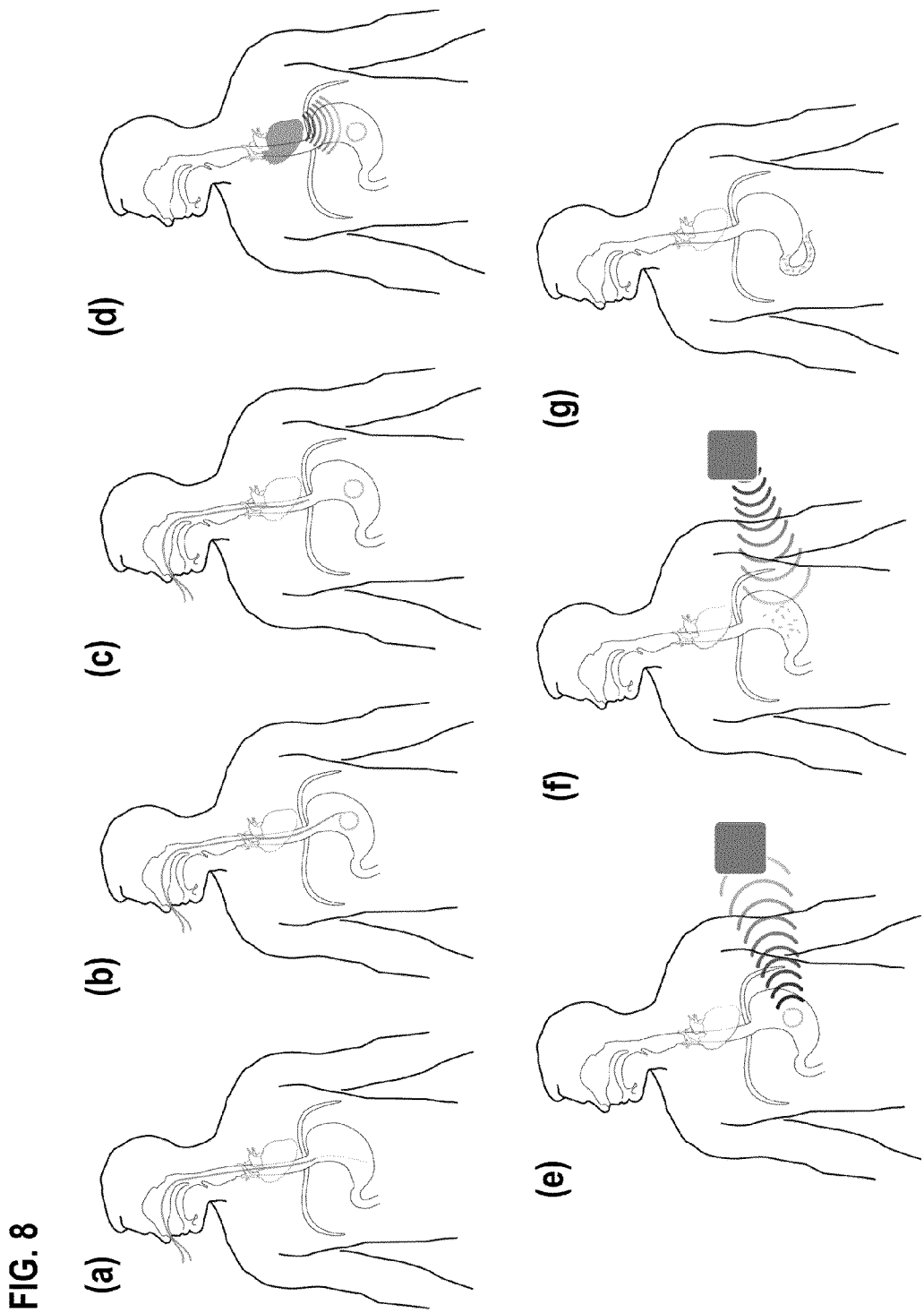
FIGS. 8($a$)-8($g$) are schematic diagrams of an entire cycle including implantation, usage, and deactivation of a monitoring apparatus, according to an embodiment of the invention.

The device in the form of a flexible delivery tube portion that is mechanically attached to the detachable device portion is first advanced through an orifice, such as a patient's nose or mouth, through their esophagus, and into the stomach cavity, as shown in FIG. 8(a). Once within the stomach, the detachable portion, which is comprised of one or more interconnecting modules, is locked in the shape of a ring as shown in FIG. 8(b), and then mechanically released from the delivery portion of the device and deployed into the stomach cavity as shown in FIG. 8(c). Inside the stomach cavity, the device is able to sense and record various physiological conditions, such as cardiac sounds from the heart as shown in FIG. 8(d), and process the data recorded. Additionally, the device can also transmit data to an external device for download and further processing, as shown in FIG. 8(e). Deactivation of the device can occur through a user-triggered signal that is communicated to the device, for example from an external device as shown in FIG. 8(f), to activate the mechanical cutting of the interconnecting region between modules. This allows the device to break apart into individual modules (see, FIG. 8(f)) that can then travel along the GI tract as shown in FIG. 8(g) through natural peristaltic motion and out of the person's body.

While the invention has been discussed with reference to cardiac monitoring, one or more aspects of the invention would be applicable to a wide variety of physiological monitoring in addition to those described in the exemplary embodiments.

It should be noted that the exemplary embodiments depicted and described herein set forth the preferred embodiments of the present invention, and are not meant to limit the scope of the claims hereto in any way. Numerous modifications and variations of the present invention are possible in light of the above teachings. It is therefore to be understood that, within the scope of the appended claims, the invention can be practiced otherwise than as specifically described herein.

What is claimed is:

1. A monitoring apparatus comprising:
a plurality of modules connected in series configured to be provided within a target cavity or lumen of a body,
wherein one or more of the plurality of modules is configured to continuously monitor physiological conditions of the body, and
wherein the plurality of modules are configured to be provided
in a first state in which each of the plurality of modules is locked to another one or more of the plurality of modules to form a closed ring shape and said monitoring apparatus is configured to remain within the target cavity or lumen without fixing to a wall of the target cavity or lumen, and
in a different second state in which the plurality of modules separate from each other and said monitoring apparatus is configured to exit the target cavity or lumen, and
wherein a state indicates a form of a collection of the plurality of modules.

2. The monitoring apparatus according to claim 1, wherein said one or more modules are configured to be provided in a third state in which said monitoring apparatus is configured to be inserted within the target cavity or lumen.

3. The monitoring apparatus according to claim 1, wherein said one or more modules are configured to transform into said second state based upon a signal generated from a component within said one or more modules.

4. The monitoring apparatus according to claim 1, wherein said one or more modules includes a module configured to wirelessly transmit and receive communications from an external device provided outside of the body.

5. The monitoring apparatus according to claim 4, wherein said one or more modules are configured to transform into said second state based upon a signal from the external device.

6. A method comprising:
providing a monitoring apparatus including a plurality of modules connected in series within a target cavity or lumen of a body, wherein the plurality of modules are provided within the target cavity or lumen in a first state in which each of the plurality of modules is locked to another one or more of the plurality of modules to form a closed ring shape and the monitoring apparatus is configured to remain within the target cavity or lumen without fixing to a wall of the target cavity or lumen;

monitoring physiological conditions of the body using one or more sensors within one or more of the plurality of modules; and providing the one or more modules in a different second state in which the plurality of modules separate from each other and the monitoring apparatus is configured to exit the target cavity or lumen, wherein a state indicates a form of a collection of the plurality of modules.

7. The method according to claim 6, wherein the monitoring apparatus is implanted within the target cavity or lumen with the one or more modules in a third state in which the monitoring apparatus is configured to be inserted into the target cavity or lumen.

8. The method according to claim 7, wherein the monitoring apparatus is implanted within the target cavity or lumen using a delivery portion, wherein the monitoring apparatus is detachably attached to the delivery portion in the third state during implantation into the target cavity or lumen, wherein the delivery portion is used to transform and lock the monitoring apparatus into the first state within the target cavity or lumen, and wherein the delivery portion is used to detach the monitoring apparatus from the delivery portion within the target cavity or lumen.

9. The method according to claim 6, wherein the one or more modules are provided into the second state based upon a signal generated from a component within the one or more modules.

10. The method according to claim 6, wherein the one or more modules includes a module that is configured to wirelessly transmit and receive communications from an external device provided outside of the body.

11. The method according to claim 10, further comprising receiving a signal at the module from the external device, wherein the one or more modules are provided into the second state based upon the signal received from the external device.

12. The method according to claim 10, further comprising transmitting data regarding the monitored physiological conditions of the body to the external device from within the target cavity or lumen.

* * * * *